United States Patent [19]

Braun

[11] 4,391,776

[45] Jul. 5, 1983

[54] DISSOCIATION CHAMBER AND MEASURING CELL COMBINATION USEFUL FOR MAKING MEASUREMENTS

[75] Inventor: Klaus Braun, Uberlingen-Bambergen, Fed. Rep. of Germany

[73] Assignee: Bodenseewerk Perkin-Elmer & Co. GmbH, Fed. Rep. of Germany

[21] Appl. No.: 223,069

[22] Filed: Jan. 6, 1981

[30] Foreign Application Priority Data

Jan. 12, 1980 [DE] Fed. Rep. of Germany ....... 3001053

[51] Int. Cl.³ ............................................. G01N 21/76
[52] U.S. Cl. .................................... 422/78; 250/373; 422/80; 422/52; 436/73; 436/172
[58] Field of Search ....................... 422/52, 54, 78, 80, 422/91, 199, 196, 197; 250/373; 23/230 PC, 232; 436/73, 172

[56] References Cited

U.S. PATENT DOCUMENTS

| | | | |
|---|---|---|---|
| 3,475,131 | 10/1969 | Keulemans | 422/80 |
| 3,581,085 | 5/1971 | Barrett | 250/373 |
| 3,704,097 | 11/1972 | Capuano | 23/230 PC |
| 3,917,404 | 11/1975 | Heiss | 250/373 |
| 3,970,430 | 7/1976 | Reader, Jr. et al. | 23/232 R |
| 3,973,910 | 8/1976 | Fine | 23/230 R |
| 4,208,372 | 6/1980 | Huber | 23/230 R |
| 4,260,890 | 4/1981 | Wright et al. | 250/373 |
| 4,311,485 | 1/1982 | Saltzman | 422/80 |

OTHER PUBLICATIONS

Tsujii et al.; Anal. Chim. Acta 97 (1978) pp. 51–57.
Bull. Chem. Soc. Japan 51(7)2020–2024, 2046–2051 (1978).

*Primary Examiner*—Michael S. Marcus
*Attorney, Agent, or Firm*—S. A. Giarratana; F. L. Masselle; R. A. Hays

[57] ABSTRACT

A dissociation chamber and measuring cell combination which is useful for making atomic fluorescence measurements includes a heated dissociation chamber and a measuring cell separate therefrom. The combination is particularly useful for use with elements which form hydrides of the sought element.

16 Claims, 10 Drawing Figures

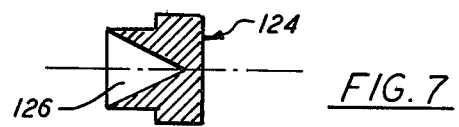
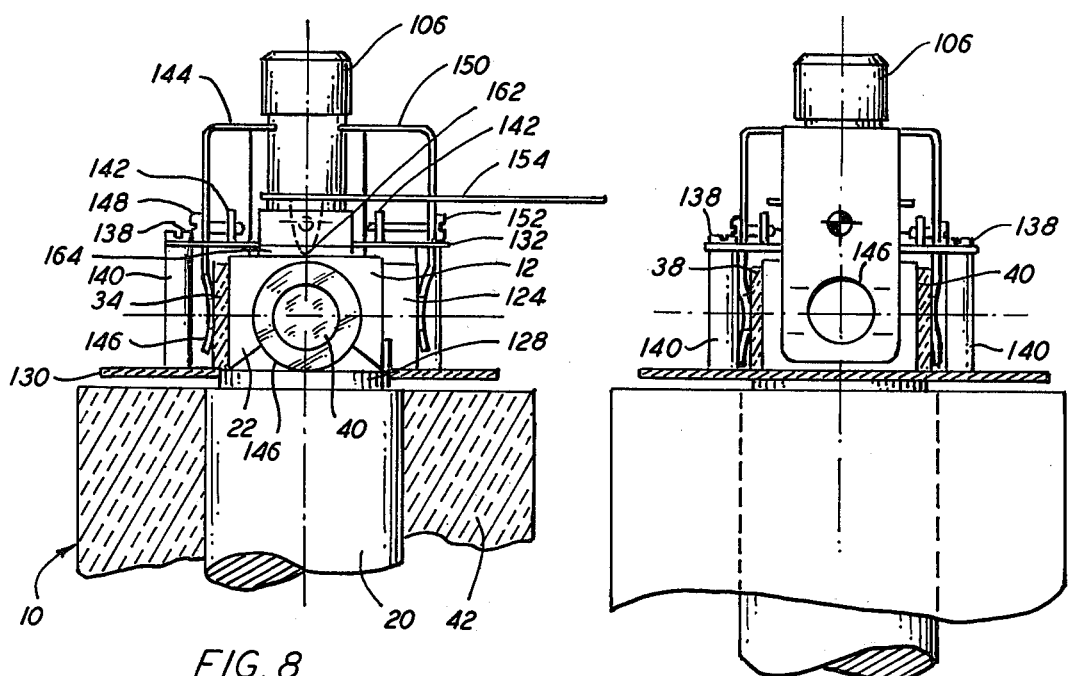
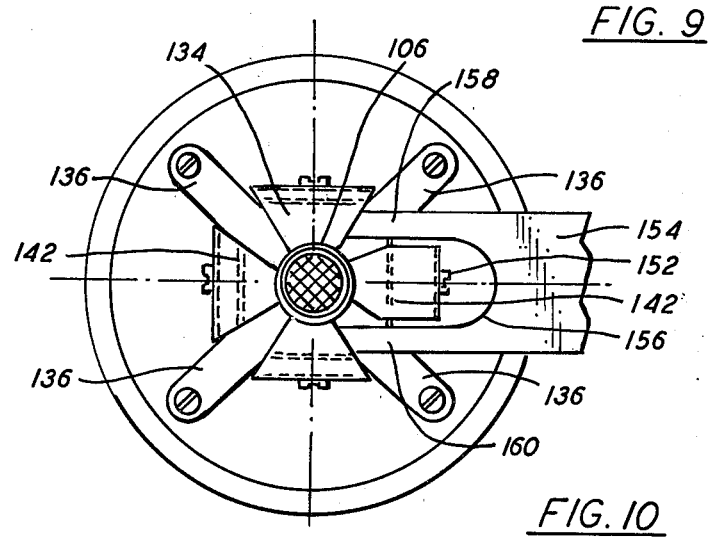

DISSOCIATION CHAMBER AND MEASURING CELL COMBINATION USEFUL FOR MAKING MEASUREMENTS

BACKGROUND OF THE INVENTION

The present invention generally relates to a dissociation chamber and measuring cell arrangement useful for making atomic fluorescence measurements. Volatile hydrides of a sought element are generated and flamelessly decomposed. In particular, the invention relates to such a combination wherein the dissociation chamber is heated and separated from the measuring cell.

It is known to determine elements, i.e. those which form voltatile hydrides such as selenium, by adding a reagent to a sample solution. In such an instance, the addition of the reagent causes the hydride of the sought element to be formed and drives it from the solution. This volatile hydride is usually guided by an inert gas flow into a heated measuring cell. Conventionally, the hydride is thermically decomposed in the heating measuring cell, whereby the element sought exists as free atoms. In practice, the measuring light beam of an atomic absorption spectrometer is passed through the heated measuring cell and the proportion of the sought element in the sample is determined from the degree of absorption of the measuring light beam. In an atomic absorption spectrometer the measuring light beam is usually produced by a light source the spectrum of which includes the line spectrum of the sought element.

Such an arrangement is known, for example, U.S. Pat. No. 4,208,372 issued to Bernard W. Huber on June 17, 1980.

In conventional arrangements the atomic absorption is measured in the measuring cell. As well known, the atoms in the measuring cell resonantly absorb light quanta from the measuring light beam of the atomic absorption spectrometer. The absorbed light quanta are subsequently emitted as resonance fluorescence. The fluorescence radiation so generated in equally distributed to all directions. In the direction of the measuring light beam the resonance absorption appears as an attenuation of the measuring light beam. The measurement of interest then is the degree or amount of attenuation of the intensity of the measuring light beam.

To increase the sensitivity and the accuracy of measurement it is known in the art to ignore the attenuation of the measuring light beam and observe the fluorescence radiation from a direction perpendicular to the measuring light beam. This radiation is proportional to the quantity of the sought element in the sample. A detector so positioned is not exposed to the comparatively high intensity measuring light beam but only to the comparatively lower intensity fluorescence radiation.

In one known arrangement (K. Tsujii and K. Kuga "Improvements in the Non-Dispersive Atomic Fluorescence Spectrometer Determination of Arsenic and Antimony by a Hydride Generation Technique" in Analytica Chimica Acta 97,51 to 57: 1978) hydrides of a single element sought in the sample, are guided into a flame, the hydrides are dissociated and free atoms of the sought element are formed. An excitation light beam is then directed through the flame, which beam also emerges from a light source emitting the line spectrum of the looked-for element. The fluorescence radiation is observed perpendicular to the direction of the excitation light beam by means of a photomultiplier.

This arrangement suffers from the disadvantage that the fluorescence signal carries with it a rather high noise background. Furthermore, non-specific fluorescence signals are observed, which signal appears to arise from OH-ions and thus reduce the accuracy of the measurement.

In another known arrangement (T. Nakahara, T. Tanaka and S. Musha "Flameless Atomic Fluorescence Spectrometry of Mercury by Dispersive and Non-Dispersive Systems in Combination with Cold-Vapor Technique" in Bulletin of the Chemical Society of Japan, volume 51(7) 2046 to 2051, 1978), where mercury is determined by measurement of the resonance fluorescence mercury vapor is driven off from a sample solution by a reagent. The vapor is guided through a heated measuring cell. The measuring cell in this arrangement is block shaped. An excitation light beam, containing therein the line spectrum of mercury, is directed through the measuring cell via windows in opposing sides thereof. The resultant fluorescence radiation is measured through a window which is perpendicular to the excitation light beam by use of a photomultiplier.

From a paper by T. Nakahara, T. Tanaka and S. Musha "Non-Dispersive and Dispersive Atomic Fluorescence Spectrometry of Arsenic by Utilizing the Arsine-generation Technique" in "Bulletin of the Chemical Society of Japan" volume 51(7), 2046-2051: 1978 an apparatus for the determination of arsenic is known. The arsenic is driven from the sample as volatile hydrides by the addition of reagents. This hydride is carried, via an inert gas flow, into the flame of a burner. The arsine is dissociated in the flame such that the arsenic exists in atomic form. A light beam, containing the resonance lines of arsenic, is directed through the flame into a substantially black body, i.e. a cavity, having low reflectance waves. The resonance fluorescence is again observed perpendicular to the direction of the light beam by means of a photomultiplier.

SUMMARY OF THE INVENTION

In view of the foregoing, it is one object of the present invention to provide a combination dissociation chamber and measuring cell for the measurement of the atomic fluorescence of hydride forming elements where the noise background of the fluorescence signal is decreased compared with prior art arrangements. This object is achieved by providing a heated dissociation chamber which chamber permits hydrides to be passed therethrough via an inert gas flow, and a measuring cell arranged downstream of the dissociation chamber which cell is adapted for observing fluorescence radiation.

Other objects and advantages of the present invention will become apparent from the following detailed specification and drawing.

BRIEF DESCRIPTION OF THE DRAWING

An embodiment of the invention is hereinafter described with reference to the accompanying drawing; which drawing is not drawn to scale and wherein:

FIG. 7 is a plug, useful as a "light trap", located at the exit side in the path of rays of the excitation light beam.

FIG. 8 is a side-elevational view of another embodiment of a measuring cell embodying the principles of the present invention.

FIG. 9 is a side-elevational view of the measuring cell viewed from the left in FIG. 8; and FIG. 10 is a plan view of the measuring cell shown in FIGS. 8 and 9.

DETAILED DESCRIPTION OF THE INVENTION

Figure 1:
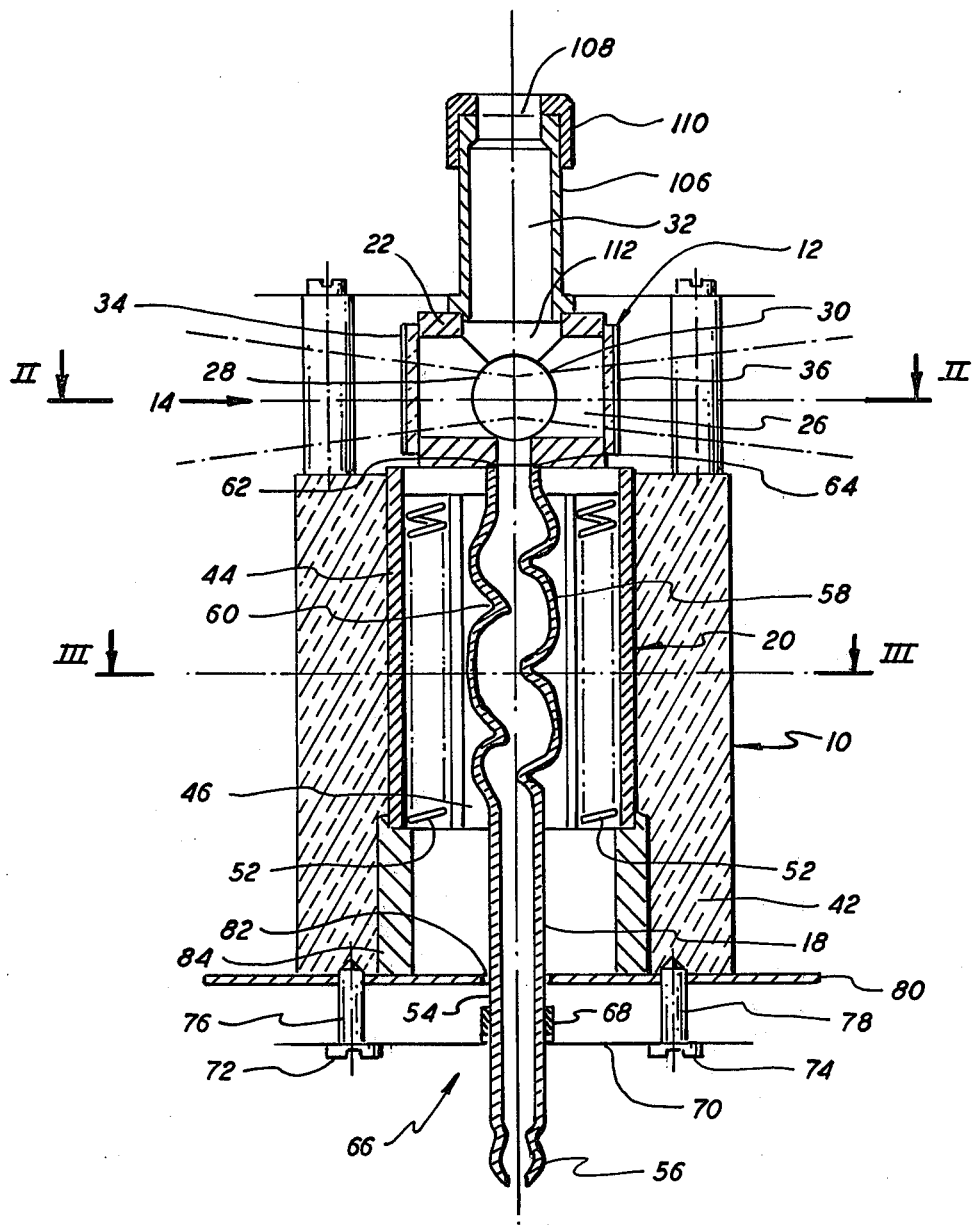
FIG. 1 is a cross-sectional view of a combination dissociation chamber and measuring cell embodying the principles of the present invention.

A heated dissociation chamber, generally indicated at 10 in FIG. 1 and embodying the principles of the present invention, permits hydrides to be passed therethrough in an inert gas flow. A measuring cell 12 separate from the heated dissociation chamber 10 and arranged downstream thereof is adapted for passing an excitation light beam 14 therethrough for observing fluorescence radiation 16 (see FIG. 2).

In one embodiment, the dissociation chamber 10 includes a tubular portion 18 surrounded by a jacket-shaped heater 20. The measuring cell 12 is preferably block-shaped, that is, a parallelepipedal body 22 having three mutually perpendicular bores 24, 26, and 28 therein. The three bores 24, 26 and 28 intersect in a measuring chamber 30.

The first bore 24 is formed as a through-bore and communicates on one side with the tubular part 18 of the dissociation chamber 10 and, on the other side, with an outlet 32. The second bore 26 is formed as a through-bore and is closed on both sides by windows 34 and 36. The excitation light beam 14 passes through the windows 34, 36 and the second through-bore 26. The third bore 28 is preferably formed as a through-bore in the illustrated embodiment and closed on both sides by windows 38 and 40. Fluorescence radiation 16 within the cell 12 is observable through the window 40. If desired, a mirror can be positioned behind the window 38 to improve the output of fluorescence radiation. The bore 28 could also be closed on the side of the window 38 and thus be open to one side only.

In the illustrated embodiment the measuring cell 12 is directly adjacent the tubular part 18 of the dissociation chamber 10. The first bore 24 of the measuring cell 12 is aligned with the tubular part 18. The dissociation chamber 10 is in heat exchange relationship with the heater 20 and is adapted to be heated to a temperature sufficiently great so as to prevent the recombination or condensation of the atoms. The heater 20 is surrounded by a heat insulating jacket 42.

Preferably, the tubular part 18 is a quartz tube which is arranged to be heated primarily via the radiation emitted by the heater 20. To that end, the heater 20 preferably has a cylindrical heating body 44 having a concentric bore 46. A circular array of axial bores 48 is provided in the heating body 44 in a regularly spaced arrangement around the concentric bore 46. The axial bores communicate with the concentric bore 46 through radial longitudinal slots 50. Heating coils 52 are arranged in the axial bores 48. The tubular part 18 also contains an inlet tube 54 having a hose connection 56 and a dissociation zone 58, which tube 54 is located inside the heating body 44. The quartz tube 18 is provided in the dissociation zone 58 with inward projections 60 which are regularly distributed over its peripheral surface. These inward projections can be formed, for example, in the way of vigreux-columns used as fractionating columns.

Heat from the heater 20 is transmitted substantially as radiation to the tubular portion 18. The heater 20, having heating coils 52 arranged in the axial bores 48, acts like a cavity radiator. The inward projections 60 act as cavities, wherein the radiation is emitted. At the inward projections 60, heat is directly transmitted to the gas passing through the tubular body 18. Furthermore, the inward projections 60 have the effect of making the gas passing therethrough turbulent, which turbulence assures substantially uniform heating of the gas.

It has been determined that an increase of the temperature in the tubular portion 18 from 750° to 900° C. does not increase the intensity of the fluorescence radiation. Therefore, it can be concluded that substantially complete dissociation of the hydrides is achieved by the above-described combination.

The measuring cell 12, in one embodiment thereof, has a concave spherical, or funnel shaped, ground surface 62 on one side of the first bore 24. The tubular portion 18 engages the ground surface 62 of the measuring cell 12 with a ground surface 64 complementary thereto at its outlet end. Axially resilient means 66 are provided which engage the tubular portion 18 and retain its ground surface 64 in resilient engagement with the ground surface 62 of the measuring cell 12. A clamp collar 68 is located on the tubular portion 18 at its inlet end. The resilient means 66 are formed, for example, by a bending spring 70 retained by a bias between the clamp collar 68 which engages the middle of the bending spring 70 and two stops, 72 and 74, which engage the other side at the ends of the bending spring 70. The stops 72 and 74 can be formed by the heads of the screws 76 and 78 located in a base plate 8. Symmetrical to the tubular portion 18. The inlet tube 54 is guided through an aperture 82 of the base plate 80.

Thus, an airtight connection is formed between the tubular portion 18 and the measuring cell 12 without unduly mechanically loading the tubular portion 18. This consideration is especially important to compensate for changes of temperature and differences of the temperature between the dissociation chamber 10 and the measuring cell 12.

As can be seen from FIG. 1, the heater 20 is supported on the base plate 80 through a jacket 84 which has a relatively low heat conductivity. The jacket 84 is preferably surrounded by heat insulation 42.

Figure 2:
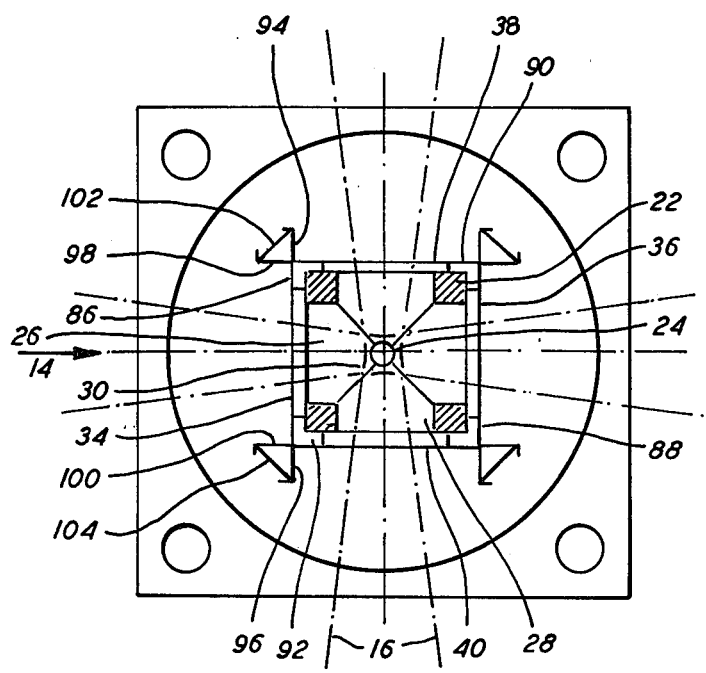
FIG. 2 is a cross-sectional view of the measuring cell of FIG. 1 as taken along line II—II thereof.
Figure 4:
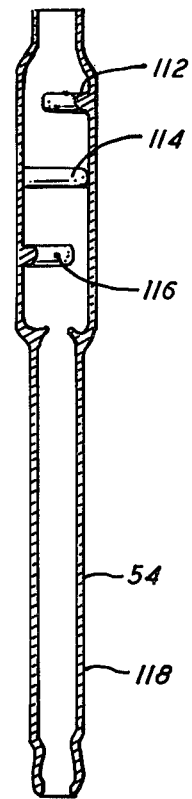
FIG. 4 is a longitudinal sectional view of a portion of the dissociation chamber.

Preferably, the windows 34, 36, 38, and 40 are retained in engagement with the polished side faces of the block-shaped body 22 by leaf springs 86, 88 and 90, 92, see FIG. 2. The leaf springs 86, 88, 90, and 92 can extend over the entire outer surfaces of the windows 34, 36, 38 and 40 respectively. However, apertures must then be provided in the leaf springs for the passage of the excitation light beam 14 and the fluorescence radiation 16, respectively. The apertures also serve as light stops in the paths of rays of the excitation light beam 14 and of the fluorescence radiation 16, respectively. In one embodiment, the leaf springs 86, 88, 90, and 92 have lateral extensions, for example 94, 96 and 98 and 100 respectively, which are angled at their ends. The extensions of each leaf spring extend laterally beyond the engaging leaf springs for example 90, 92 so that the leaf springs 86 and 90, 92 cross with their extensions 94, 98 and 90, 100 respectively. One connecting link each 102, 104 is retained under bias between the angled ends of the engaging, mutually perpendicular extensions 94, 98 and 96, 100 respectively.

The block-shaped body 22 of the measuring cell 12 can be fabricated from glass ceramics, tightly sintered oxide ceramics, quartz ceramics, or the like.

The outlet 32 communicating with the first bore 24 of the measuring cell 12 can be formed by an outlet tube 16 having a relatively large cross-section compared to the first bore 24 and connected thereto. Referring to FIG. 1, outlet tube 106 is preferably closed by a wire grating 108 retained by a cap 110. The first bore 24 widens at 112 to about the diameter of the outlet tube 106. The exit opening 112 and the outlet tube 106, which outlet tube 106 is arranged in extension of the first bore 24, effect a substantially non-turbulent flow inside the measuring cell 12. The wire grating 108 is adapted to extract enough heat from the gas passing therethrough so that the hydrogen is not inflamed upon exiting into the atmosphere.

In the embodiment shown in FIGS. 1 and 2, the aligned windows 34 and 36 which are provided for the excitation light beam 14 are arranged such that the excitation light beam 14 passes through the measuring cell 12. Vagrant stray radiation which may occur due to radiation is reflected or scattered on the exit side of the window 36.

Alternatively, the window 36 can be omitted and a plug 124 (see FIG. 7) can be inserted into the exit end of the bore for preventing vagrant radiation reflection. The plug 124 acts as a light absorber, which to a large extent absorbs the excitation light beam 14 after it has passed through the measuring cell 12. In the embodiment of FIG. 7 the plug 124 facing the inside of the measuring cell 12 has a tapered cavity 126. The angle of the taper is selected so that no directionally reflected portion of the excitation light beam 14 escapes the cavity 126.

To this end, and to maintain the diffusely reflected radiation to a minumum, the plug 124 is preferably made of a material having a low remissivity. Black quartz glass or darkly inked cermics are advantageous for use in the rather high temperatures which occur. Black quartz glass is a transparent quartz glass made opaque by finely dispersed carbon and having the same qualities. Other shapes can also be used instead of a tapered cavity. It has been found, however, that stray light cannot be eliminated completely even with an absorber of the described type. For instance, stray light can also arise from impurities, scratches or the like on the window 34 on the entrance side, stop edges, mounting parts and so on and thereby gain entrance into the measuring cell and impinge on the detector as vagabond radiation. For effectively weakening this vagabond radiation it is advantageous to make the entire body 22 of a material with a low remissivity material. Advantageously a similar material can be used for the body 232 as is used for the plug 124, that is a black quartz glass or darkly inked ceramics.

Figure 3:
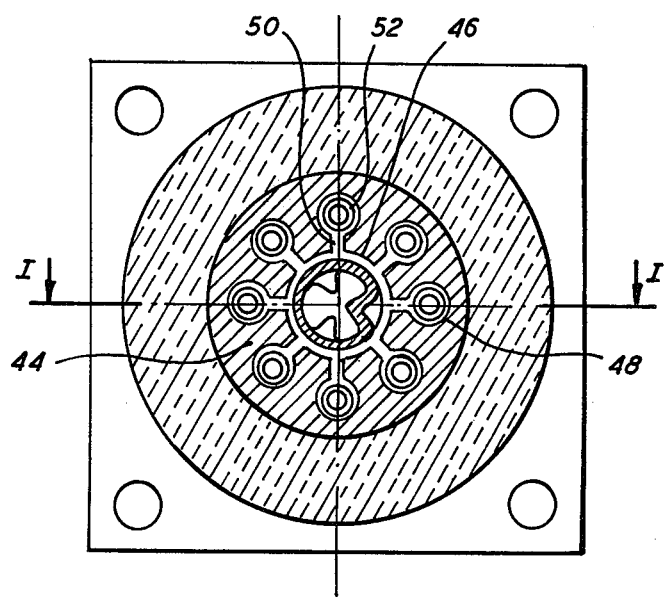
FIG. 3 is a cross-sectional view of the dissociation chamber of FIG. 1 as taken along the line III—III thereof.
Figures 5, 6:
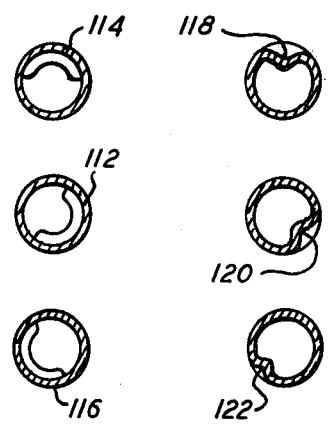
FIG. 5 is a cross-sectional view of the tubular part of FIG. 4 taken in different planes thereof.
FIG. 6 is a cross-sectional view of a tubular part in different planes of another embodiment.

In the embodiment shown in FIGS. 1, 2 and 3, a single window 34, 36, 38 or 40 cannot be changed without dismantling the whole measuring cell 12. However, an arrangement such as that shown in FIGS. 8, 9 and 10 substantially eliminates these problems.

In the embodiment shown in FIGS. 8, 9 and 10 a measuring cell 12 is located on a dissociation chamber 10 and connected thereto in a similar way as in the embodiment of FIG. 1. Numeral 34 designates a window on the entrance side for the extraction light beam. A plug 124 is placed opposite to the window 34 in the bore according to FIG. 7, which plug 124 serves as "light trap" for the excitation light beam. The windows 38 and 40 are retained in engagement with the body 22 perpendicular thereto. An outlet tube is vertically positioned on the parallelepipedal body 22.

The upper end 128 of the heater 20 extending out of the heat insulating jacket 42 of the dissociation chamber 10 is surrounded by an annular disc 130. A plate 132 is positioned above the measuring cell 12, which plate 132 has an almost rectangular central portion 134 and four radial arms 136 extending from the corners thereof, as can be seen best from FIG. 10. The ends of the arms 136 are retained at a fixed distance from the annular disc 130 by, for example, screw bolts 138 screwed into the annular disc 130 and spacer tubes 140. Thus, the plate 132 extends horizontal substantially parallel to the annular disc 130. The edges of the central portion 134 located between the arms 136 are bent upwards. L-shaped leaf springs 144 are supported with their upper, shorter legs on the outlet tube 106. The longer legs of the leaf springs 144 extend downwards and engage the windows 34, 38 and 40. The springs include apertures 146 which act as light stops for the passage of the light beams. The leaf springs 144 are biased by screws 148, which are passed through holes of the leaf springs 144 and screwed into threaded holes of the bent edges 142. Similarly, an L-shaped leaf spring 150 is provided, which is supported with its horizontal leg on the outlet tube 106 and which urges the plug 124, with the vertical leg thereof, into the bore of the body 22. This leaf spring 150 is also biased by a screw 152 threaded into a hole of the bent edge 142.

A horizontal leaf spring 154 extends with a U-shaped recess 156 around the leaf spring 150 and carries a conical projection 162, extending downwards, on each of its legs 158, 160 formed on both sides of the recess. The projections 162 extend with their points into holes of the plate 132. The plate 132 has a central aperture, through which the outlet tube 106 extends. The edge of this aperture is located on a collar 164 of the outlet tube 106. The central portion 134 of the plate 132, the outlet tube 106 and the measuring cell 12 are pressed downwards through the leaf spring 154 against the dissociation arrangement 10. In this arrangement each window can be changed individually by loosening the screw 148 and removing the respective spring 144. The mounting of the other windows is not affected thereof.

Advantageously, the present configuration permits the fluorescence radiation to be measured in a "flameless" operation, which essentially decreases the noise background. This becomes possible because the hydrides are dissociated in the insulated, heated dissociation chamber wherefrom the atoms formed therein are guided into a measuring cell separate from the dissociation chamber, which cell is adapted for the measurement of the fluorescence radiation.

Although the present invention has been described herein with reference to particular embodiments, these embodiments are intended to be exemplarly only and not limiting as to the scope or spirit of the present inven-

What is claimed is:

1. In combination, a dissociation chamber and measuring cell useful for observing fluorescence radiation, said combination comprising:
   a heated dissociation chamber adapted to permit hydrides to be passed therethrough with an inert gas flow, said dissociation chamber including a tubular part surrounded by a jacket-shaped heater, said tubular part having, on the outlet side thereof, a ground surface; and
   a measuring cell adjacent said tubular part of said dissociation chamber and located downstream thereof, said cell being adapted for passing an excitation light beam therethrough and for observing fluorescence radiation occurring therein, said measuring cell being a block-shaped body and having three mutually perpendicular bores of which:
   the first bore being a through bore communicating on one side thereof with said tubular part of said dissociation chamber and on the other side with an outlet, said first bore having a funnel-shaped ground surface on said one side thereof, said ground surface being complementary to, and engaging with, said ground surface of said tubular part;
   the second bore being a through bore closed on both sides thereof by windows whereby an excitation light beam can be passed therethrough;
   the third bore being closed by a window through which fluorescence radiation can be observed; and
   means, axially resilient and engaged with said tubular part, for retaining said ground surface thereof in resilient engagement with said ground surface of said measuring cell.

2. The combination as claimed in claim 1 further comprising:
   a clamp collar on said tubular part at the inlet end thereof; and
   said axially resilient engaging means being formed by a bending spring, said means being retained by a bias between said clamp collar engaging the middle of said bending spring and two stops engaging the other side at the ends of said bending spring.

3. The combination as claimed in claim 1 wherein said windows are retained in engagement with the polished side faces of said block-shaped body by leaf springs.

4. The combination as claimed in claim 1 wherein said measuring cell being in heat exchange relationship with a heater whereby recombination or condensation of atoms therein is prevented.

5. The combination as claimed in claim 4 wherein said heater is surrounded by a heat insulating jacket.

6. The combination as claimed in claim 1 wherein said block-shaped body of said measuring cell is made of a material with low remissivity.

7. The combination as claimed in claim 6 wherein said block-shaped body of said measuring cell is made of black quartz glass.

8. The combination as claimed in claim 6 wherein said block-shaped body of said measuring cell is made of darkly inked ceramics.

9. The combination as claimed in claim 1 wherein said outlet communicating with said first bore of said measuring cell, is formed by an outlet tube having relatively large cross-section and connected to said first bore.

10. The combination as claimed in claim 9 wherein said outlet tube is closed by a wire grating.

11. The combination as claimed in claim 1 wherein:
    said dissociation chamber has a tubular part surrounded by a jacket-shaped heater; and
    said measuring cell has a block-shaped body with three mutually perpendicular bores of which:
    a first bore is formed as through bore and communicates on one side with the tubular part of the dissociation equipment and on the other side with an outlet;
    a second bore is formed as through bore and is closed on one side by a window and on the other side by a "light trap" whereby an excitation light beam is permitted to pass through said window of said second bore and is absorbed in said "light trap", and
    the third bore is closed by a window through which fluorescence radiation can be observed.

12. The combination as claimed in claim 11 wherein:
    said light trap consists of a plug of a material with a low remissivity; and
    a cavity is formed in the end face of said plug facing the inside of said measuring cell.

13. The combination as claimed in claim 12 wherein said cavity is conical with a cone angle preventing re-exit of directionally reflected light.

14. In combination, a dissociation chamber and measuring cell useful for observing fluorescence radiation, said combination comprising:
    a heated dissociation chamber adapted to permit hydrides to be passed therethrough with an inert gas flow, said dissociation chamber including a quartz tubular part surrounded by a jacket-shaped heater, said quartz tube includes a plurality of inward projections regularly distributed over the peripheral surface thereof;
    a measuring cell separated from said dissociation chamber and located downstream thereof, said cell being adapted for passing an excitation light beam therethrough and for observing fluorescence radiation occuring therein, said measuring cell being a block-shaped body having three mutually perpendicular bores, of which:
    the first bore being a through bore communicating on one side thereof with said tubular part of said dissociation chamber and on the other side with an outlet;
    the second bore being a through bore closed on both sides thereof by windows whereby an excitation light beam can be passed therethrough; and
    the third bore being closed by a window through which fluorescence radiation can be observed.

15. The combination as claimed in claim 14 wherein said quartz tube is arranged to be heated by radiation emitted by said heater.

16. The combination as claimed in claim 15 wherein:
    said heater having a cylindrical heating body with a concentric bore for accommodating said quartz tube;
    said heating body having a circular array of axial bores in regular arrangement around said concentric bore, said axial bores communicating with said concentric bore through radial longitudinal slots; and
    heating coils being arranged in said axial bores.

* * * * *